United States Patent [19]

Imai et al.

[11] Patent Number: 4,933,289

[45] Date of Patent: Jun. 12, 1990

[54] **BIOLOGICALLY PURE CULTURES OF *PSEUDOMONAS SORBOSOXIDANS* USEFUL FOR PRODUCING 2-KETO-L-GULONIC ACID**

[75] Inventors: Ko Imai, Minoo; Takeshi Sakane, Suita; Ikuo Nogami, Nagaokakyo, all of Japan

[73] Assignee: Takeda Chemical Industries, Ltd., Osaka, Japan

[21] Appl. No.: 413,384

[22] Filed: Sep. 27, 1989

Related U.S. Application Data

[62] Division of Ser. No. 57,979, Jun. 4, 1987.

[30] Foreign Application Priority Data

Jun. 5, 1986 [JP] Japan .................................. 61-131121

[51] Int. Cl.⁵ .......................... C12R 1/38; C12P 7/60
[52] U.S. Cl. ................................. 435/253.3; 435/138; 435/874
[58] Field of Search ....................... 435/138, 253,3, 874

[56] References Cited

U.S. PATENT DOCUMENTS

| | | | |
|---|---|---|---|
| Re. 30,872 | 2/1982 | Sonoyama et al. | 435/138 |
| 2,277,716 | 3/1942 | Lockwood et al. | 425/138 |
| 2,917,435 | 12/1959 | Perlman | 435/138 |
| 3,043,749 | 7/1962 | Huang | 435/138 |
| 3,959,076 | 5/1976 | Sonoyama et al. | 435/138 |
| 3,963,574 | 6/1976 | Sonoyama et al. | 435/138 |
| 3,992,194 | 11/1975 | Sonoyama et al. | 435/138 |
| 4,155,812 | 5/1979 | Kita | 435/138 |
| 4,245,049 | 1/1981 | Kita et al. | 435/138 |
| 4,876,195 | 10/1989 | Shirafuji et al. | 435/138 |
| 4,877,735 | 10/1989 | Nogami et al. | 435/138 |
| 4,879,229 | 11/1989 | Sonoyama et al. | 435/138 |

FOREIGN PATENT DOCUMENTS 0221707  5/1987  European Pat. Off. ............ 435/138

*Primary Examiner*—Herbert J. Lilling
*Attorney, Agent, or Firm*—Wenderoth, Lind & Ponack

[57] ABSTRACT

2-Keto-L-gulonic acid is produced in a high yield by contacting L-sorbose with a microorganism of *Pseudomonas sorbosoxidans*, or a processed material thereof.

5 Claims, No Drawings

BIOLOGICALLY PURE CULTURES OF *PSEUDOMONAS SORBOSOXIDANS* USEFUL FOR PRODUCING 2-KETO-L-GULONIC ACID

This application is a division of application Ser. No. 057,979, filed Jun. 4, 1987.

FIELD OF THE INVENTION

The present invention relates to a method for producing 2-keto-L-gulonic acid which is useful as a precursor for the synthesis of vitamin C (L-ascorbic acid) and a novel microorganism belonging to the genus Psuedomonas to be used in said production method.

BACKGROUND OF THE INVENTION

2-Keto-L-gulonic acid which is useful as a precursor for the synthesis of vitamin C has been industrially produced by the Richstein method [Helvetica Chimica Acta 17, 311 (1934)]. However, this method involves many steps, and improvement in total yield can not be expected. Therefore, it is desired to find out more effective production methods.

Instead of the Reichstein method, a method which comprises producing 5-keto-L-gluconic acid from glucose microbiologically, converting it into idonic acid chemically or microbiologically, and then oxidizing the resultant to give 2-keto-L-gulonic acid (U.S. Pat. No. 2,421,611), and a method which comprises producing 2,5-diketo-D-gluconic acid from glucose microbiologically and reducing the resultant to 2-keto-L-gulonic acid chemically or microbiologically (Japanese Patent Publication Nos. 39-14493, 53-25033, 56-15877 and 59-35920) have been studied. However, the chemical reduction steps employed in these methods, are not stereospecific, and the former provides D-gluconic acid and the latter provides 2-keto-D-gluconic acid as by-products, which results in a decrease in yield. Further, when this step is carried out microbiologically, excessive carbon source should be supplied as a reduction energy source.

Also, the method for production of 2-keto-L-gulonic acid using L-sorbose as a starting material has been known. In this case, the product can be produced only by an oxidation step without involving any reduction step. As examples of this method, the methods using bacteria belonging to the genera Gluconobacter, Pseudomonas, Serratia, Achromobacter and Alcaligenes, have been heretofore known [see Biotechnology and Bioengineering 14, 799 (1972), Acta Microbiological Sinica, 20, 246 (1980) and 21, 185 (1981), Japanese Patent Publication Nos. 41-159 and 41-160, U.S. Pat. No. 3,043,749, Japanese Patent Publication No. 49-39838 and U.S.S.R. Patent No. 526,660]. However, the methods for production of 2-keto-L-gulonic acid from L-sorbose by strains which have been disclosed give extremely low product yield, and they can not be industrially utilized.

One improvement of these known methods by using a microorganism belonging to the genus Pseudogluconobacter is disclosed in the co-pending U.S. patent application Ser. No. 913,230 filed Oct. 1, 1986 which has been assigned to the same assignee as that of the present application.

OBJECTS OF THE PRESENT INVENTION

In order to obtain a strain which can produce 2-keto-L-gulonic acid from L-sorbose in a high yield, the present inventors have isolated various strains from soil samples collected in Japan and screened them. As the result, three strains which give extremely higher yield than the earlier results (about 80% based on the sugar consumed) i.e. isolated No. 526-21, No. 526-22 and No. 526-42 have been found. The present inventors have studied these three strains intensively, and found that they belong to a novel species of the genus Pseudomonas. Thus, the present invention is attained.

SUMMARY OF THE INVENTION

That is, the present invention provides a method for producing 2-keto-L-gulonic acid which comprises contacting L-sorbose with a microorganism of *Pseudomonas sorbosoxidans* having an ability to oxidize L-sorbose to 2-keto-L-gulonic acid or a processed material thereof to produce and accumulate 2-keto-L-gulonic acid, and harvesting it. Further, the present invention provides a novel bacterial species, *Pseudomonas sorbosoxidans* which is a motile rod bacterium having two or more polar flagella, and which produces no dihydroxyacetone from glycerol, contains ubiquinone having 10 isoprene units, and requires thiamine, riboflavine and pantothenic acid for its growth.

DETAILED DESCRIPTION OF THE INVENTION

The three strains which the present inventors have found have the following taxonomic characteristics.

(a) Morphological characteristics:
 (1) Rods, 0.3 to 0.5×0.7 to 1.4 μm.
 (2) No cellular polymorphism observed.
 (3) Having motility and 2 or more polar flagella.
 (4) Non-sporulating.
 (5) Gram-negative.
 (6) Non-acid-fast.

(b) Cultural characteristics:
 (1) Nutrient agar plate: moderate growth; round, entire, smooth and milk-white colonies.
 (2) Nutrient ager slant: moderate growth; filiform, smooth, milk-white.
 (3) Nutrient liquid culture: moderate growth with precipitates.
 (4) Nutrient gelatin stab culture: growth only at upper portion without liquefaction of gelatin.
 (5) Litmus milk: acidified, not coagulated, not decomposed.

(c) Physiological characteristics:
 (1) Nitrate reduction: weakly positive.
 (2) Denitrification: negative.
 (3) Methyl red (MR) test: slightly positive.
 (4) Voges-Proskauer (VP) test: slightly positive.
 (5) Indole: not produced.
 (6) Hydrogen sulfide: not produced.
 (7) Starch hydrolysis: negative.
 (8) Citrate utilization: negative.
 (9) Ammonium salts: utilized as nitrogen source.
 (10) Pigments: not produced.
 (11) Urease: positive.
 (12) Oxidase: positive.
 (13) Catalase: positive.
 (14) The strain can grow at 15° to 36° C. The optima; growth temperature is about 30° C. The strain can grow at pH 5.5 to 8.7. The optimum growth pH is 6.0 to 7.5.
 (15) Aerobic.
 (16) Hugh-Leifson's OF test: oxidative.
 (17) Acid is slightly produced but gas is not produced from L-arabinose, D-xylose, D-glucose, D-mannose, D-fructose, D-galactose, maltose, sucrose, lactose, and trehalose. Neither acid nor gas is produced from D-sorbitol, D-mannitol, inositol, glycerol, and starch.

(d) Other characteristics:

(1) The content of guanine and cytosine of DNA: about 67 mole %.

(2) Containing ubiquinone with 10 isoprene units.

(3) Dihydroxyacetone: not produced from glycerol.

(4) Thiamine, riboflavine and pantothenic acid are essentially required for the growth. The growth is promoted by biotin and casamino acids.

The above taxonomical characteristics were reviewed by reference to Bergey's Manual of Systematic Bacteriology, Vol. 1 (1984). As the result, it is reasonably considered that all these strains are belong to the genus Pseudomonas because they are gram-negative, aerobic, motile rods with polar flagella and oxidase-positive. Since they require vitamins and amino acids for the growth and contain 67 mole % of the guanine and cytosine of DNA, they are classified as a member of Section IV of this genus. Further, since they contain ubiquinone having 10 isoprene units, it is considered that they are similar to *Pseudomonas diminuta* and *Pseudomonas vesicularis* which belong to this Section. However, they are different from above two species in view of the number of flagella, assimilability of sugars and the like, and no corresponding known species can be found in the genus Pseudomonas. Therefore, it is determined that they belong to a novel species of this genus. Then, these three strains have been named *Pseudomonas sorbosoxidans* and deposited at the Institute for Fermentation, Osaka, (IFO) on Apr. 11, 1986 and at Fermentation Research Institute of the Agency of Industrial Science and Technology, the Ministry of International Trade and Industry (FRI) on Apr. 26, 1986. The deposit in FRI has been converted to a deposit under the Budapest Treaty since Apr. 3, 1987. Isolation numbers and accession numbers of these three strains in the Depositories are as follows:

| Isolation No. | FERM | Accession No. | IFO |
|---|---|---|---|
| 526-21 | FERM P-8750 | FERM BP-1334 | IFO 14501 |
| 526-22 | FERM P-8751 | FERM BP-1335 | IFO 14502 |
| 526-42 | FERM P-8752 | FERM BP-1336 | IFO 14503 |

The strains which can be used according to the present invention include not only these three strains but also other strains of *Pseudomonas sorbosoxidans* inclusive of the mutants derived from these strains by irradiation with ultraviolet light or X-rays, or treatment with chemical mutagens such as N-methyl-N'-nitro-N-nitrosoguanidine (nitrosoguanidine), methylmethanesulfonate, nitrogen mustard and so on, as far as the strains are able to oxidize L-sorbose to 2-keto-L-gulonic acid.

As an example of such mutants, there may be mentioned the strain SB-15 which was derived from the strain 526-21 by treating with nitrosoguanidine. This mutant strain SB-15 exhibits the same taxonomical characteristics as the parent strain except that it shows an increased ability to produce 2-keto-L-gulonic acid from L-sorbose. The strain SB-15 was deposited at IFO on Apr. 23, 1987 as the accession number IFO 14604 and at FRI on May 1, 1987 as the accession number FERM BP-1356 under the Budapest Treaty.

In the method of the present invention, any of said strains can be cultivated with a medium containing L-sorbose or L-sorbose can be contacted with a processed material of said strains.

The term "processed material" used in the present invention means washed cells obtained from culture broths of any of said strains, acetone dried cells, immobilized cells on supports such as polyacrylamide gel, κ-carrageenin and the like.

The starting material, L-sorbose, can be added all at once to a medium at the beginning of cultivation, or it may be added in several installments in the course of cultivation, or continuously to the culture medium.

In the reaction wherein L-sorbose is contacted with said strain, the concentration of L-sorbose based on the medium is 3 to 30% (w/v), preferably, 5 to 25% (w/v).

As the method for contacting L-sorbose with said processed material, there can be employed, for example, a method wherein L-sorbose, 2-(N-morpholino)-ethanesulfonic acid (MES) buffer (0.5M, pH 6.5) and $CaCO_3$ are added to the processed material and the mixture is diluted with water, and shaken in a conical flask.

In the reaction wherein L-sorbose is contacted with said processed material, the concentration of L-sorbose is 0.1 to 10% (w/v), preferably 0.3 to 3% (w/v), and the amount of the processed material is 1 to 30 mg/ml, preferably 3 to 20 mg/ml, on the dried cell basis. The pH of the reaction solution is adjusted to 5.5 to 7.5 and the reaction temperature is about 20° to 40° C., the reaction time is about 1 to 100 hours.

The medium used for cultivation of said strain can be liquid or solid so far as it contains nutrient sources which can be utilized by said strains. However, a liquid medium is preferred for mass production of the objective compound. For the medium, carbon sources, nitrogen sources, inorganic salts, organic salts and trace nutrients which are used in conventional cultivation of microorganisms can be used. While the starting material, L-sorbose, can be used as the carbon source, other auxiliary carbon sources such as glucose, glycerin, sucrose, lactose, maltose, molasses, and the like can also be used. As the nitrogen sources, there can be used inorganic and organic nitrogen-containing materials such as ammonium salts, corn steep liquor, peptone, meat extract, yeast extract, dry yeast, cottonseed meal, urea and the like.

And, the inorganic salts include salts of potassium, sodium, calcium, magnesium, iron, manganese, cobalt, zinc, copper and phosphoric acid.

As the trace nutrients, there can be suitably added biotin, thiamine, riboflavine, pantothenic acid and amino acids which are essential growth factors or promoters of said strains, or natural materials containing them.

Stationary culture, shaking culture, or agitating culture with aeration can be employed as the means for cultivation. However, for mass production, the so-called submerged culture is preferred.

Cultural conditions depend on a particular strain to be used, medium composition and the like, and, briefly, they can be chosen in each case so that the objective product can be obtained with the highest efficiency. For example, cultivation is preferably carried out at 25° to 35° C., and the pH of the medium is desirably about 5 to 9. As the cultivation is conducted under the above conditions for 10 to 120 hours, 2-keto-L-gulonic acid is accumulated in the highest concentration. In this case, since the pH value of the medium generally drops as the objective compound is produced, it may be advantageous to add a suitable basic substance such as sodium hydroxide, potassium hydroxide, ammonia and the like to always maintain the optimal pH level for the microbial production of 2-keto-L-gulonic acid, or add a suitable buffer agent to maintain the optimal.

The 2-keto-L-gulonic acid thus produced and accumulated in the culture broth of the reaction mixture can be harvested and purified by a per se known method utilizing its properties. 2-Keto-L-gulonic acid may be harvested in the form of the free acid, or isolated in the form of a salt of sodium, potassium, calcium, ammonium or the like.

Any harvesting method compatible with the object of the present invention can be employed. For example, the culture broth is freed of cells, as required, by filtration, centrifugation or treatment with activated carbon and then the solution obtained is concentrated. The precipitated crystals are collected by filtration and further recrystallized to recover the objective compound. Further, precipitation, solvent extraction, chromatography or salting-out, and other procedures may be applied in a suitable combination and/or in repetition.

When 2-keto-L-gulonic acid is obtained in its free form, it can be converted to a salt of, for example, sodium, potassium, calcium, ammonium or the like by a conventional method. When it is obtained in the form of a salt, it can be converted into the free form or a different salt by a conventional method.

The objective product obtained according to the present invention has been identified as 2-keto-L-gulonic acid by the determination of physicochemical properties such as elemental analysis, melting point, optical rotation, infrared absorption spectrum and the like.

The quantitative determination of 2-keto-L-gulonic acid produced in the reaction mixture or the culture broth was performed by high performance liquid chromatography (mobile phase: diluted sulfuric acid to pH 2.2; flow rate: 0.5 ml/min.; detector: differential refractometer) using a sulfonated polystyrene gel column (manufactured by Shimadzu Seisakusho, Ltd., SCR-101H column, 7.9 mm×30 cm). As the standard, crystals of sodium 2-keto-L-gulonate monohydrate were used. The detection of 2-keto-L-gulonic acid was conducted by thin layer chromatography. As a cellulose plate (manufactured by Merck) was spotted with a sample and after development with a solvent system of phenol-water-formic acid (75:25:5) at room temperature for 3 hours, dried and treated with a color reagent, 2-keto-L-gulonic acid gave a spot with a Rf value of about 0.3, the spot being black-brown with silver nitrate, yellow with o-phenylenediamine, and pink with anilinephthalic acid.

The present invention is further illustrated in detail in the following examples. The % figures mentioned in connection with media represent weight/volume percents unless otherwise stated.

EXAMPLE 1

A 200 ml conical flask was charged with 20 ml of a seed culture medium containing 2.0% of glucose, 1.0% of polypeptone (Daigo Nutritive Chemicals, Japan), 0.5% of dried yeast and 2.0% of $CaCO_3$, and sterilized by autoclaving at 121° C. for 15 minutes. The flask was inoculated with a loopful of *Pseudomonas sorbosoxidans* 526-21 (IFO 14501; FERM P-8750; FERM BP-1334) grown at 28° C. for 2 days on a slant containing 2.0% glucose, 1% polypepton, 0.2% yeast extract, 0.5% NaCl and 1.5% agar, and incubated at 28° C. with shaking (200 rpm) for 2 days to obtain a seed culture broth.

A sterilized 200 ml-conical flask was charged with 25 ml of a fermentation medium containing 1.0% polypepton, 0.2% casamino acid (Difco Lab. U.S.A.), 0.5% dried yeast, 0.5% $(NH_4)_2SO_4$, 0.05% $Na_2S_2O_3 \cdot 5H_2O$, 0.03% $KH_2PO_4$, 0.05% $MgSO_4 \cdot 7H_2O$, 0.1% $FeSO_4 \cdot 7H_2O$, 0.0005% $MnSO_4 \cdot nH_2O$, 0.0005% thiamine hydrochloride and 6.0% $CaCO_3$ which were previously autoclaved, and 15.0% L-sorbose which was separately sterilized by filtration. This conical flask was inoculated with 2 ml of the above-obtained seed culture broth and incubated at 28° C. with shaking for 3 days. An assay by the high performance liquid chromatography showed that the resulting fermentation broth contained 54.9 mg/ml of 2-keto-L-gulonic acid (conversion ratio: 34.0% based on used sugar). This fermentation broth (1,000 ml) was centrifuged to remove the cellular and other sediments. The supernatant (about 980 ml) obtained was passed through an Amberlite IR 120 (Rhom & Haas Co., U.S.A., H-form, 500 ml) column which was then washed with about 300 ml of deionized water. The effluent and washings were combined, adjusted to pH 6.5 with sodium hydroxide, and concentrated to about 50 ml under reduced pressure at 50° C. This concentrate was allowed to stand at 5° C. for 24 hours, whereupon colorless prisms were obtained. The prisms were collected by filtration, washed with a small quantity of cold methanol, and dried over phosphorus pentoxide at room temperature under reduced pressure to give 38.5 g of monosodium 2-keto-L-gulonate monohydrate.

Melting point 147°–155° C. Elemental analysis ($C_6H_9O_7Na \cdot H_2O$) Calcd.: C, 30.78%; H, 4.74% Found: C, 30.84%; H, 4.89% Specific rotation: $[\alpha]_D^{24} -23.3°$ (C=1.0, water)

In HPLC retention time, TLC Rf value, and color reaction on TLC, the above product was in agreement with the authentic sample.

EXAMPLE 2

According to the same manner as mentioned in Example 1, a seed culture broth of *Pseudomonas sorbosoxidans* 526-22 (IFO 14502, FERM P-8751, FERM BP-1335) was prepared. Two ml of this seed culture broth was inoculated into a 200 ml-conical flask containing 25 ml of the same fermentation medium as that used in Example 1 except that the concentration of $Na_2S_2O_3 \cdot 5H_2O$ was changed to 0.1% and the flask was incubated with shaking at 30° C. for 5 days. In the resulting fermentation broth, there was contained 72.9 mg/ml of 2-keto-L-gulonic acid (conversion ratio: 45.1% based on used sugar).

EXAMPLE 3

A 200 ml-conical flask was charged with 20 ml of a seed culture medium containing 2.0% glucose, 0.3% yeast extract, 0.3% CSL, 0.5% casein, and 2.0% $CaCO_3$ and sterilized by autoclaving at 121° C. for 15 minutes. The flask was inoculated with a loopful of *Pseudomonas sorbosoxidans* 526-42 (IFO 14503, FERM P-8752, FERM BP-1336) grown on the same slant as in Example 1 at 28° C. for 2 days, and incubated at 28° C. for 1 day to obtain a seed culture broth.

A 200 ml-conical flask was charged with 20 ml of a medium containing 2.0% CSL, 0.05% $Na_2S_2O_3 \cdot 5H_2O$, 0.1% $FeSO_4 \cdot 7H_2O$, 0.3% $(NH_4)_2SO_4$, 0.0001% FMN, 0.00005% biotin and 9% $CaCO_3$ and sterilized by autoclaving. The flask was inoculated with 2 ml of the above-obtained seed culture broth and incubated with shaking at 30° C. for 3 days with addition of a 40% aqueous solution of L-sorbose sterilized by filtration in such amounts and time intervals as 3 ml immediately after inoculation, 3 ml after 16 hours, 2 ml after 40 hours and 3 ml after 48 hours, respectively. As assayed by HPLC, the resulting fermented broth thus obtained contained 85.4 mg/ml of 2-keto-L-gulonic acid (conversion ratio: 50.3% based on used sugar; 86.0% based on consumed sugar).

EXAMPLE 4

The fermented broth of *Pseudomonas sorbosoxidans* 526-21 (1,000 ml) as obtained in Example 1 was centrifuged and the resulting precipitate was suspended in a cold physiological saline solution (0.85%). The suspension was centrifuged at 1,000 rpm for 5 minutes to remove a precipitate mainly composed of $CaCO_3$. The supernatant was further centrifuged at 9,000 rpm for 10 minutes to obtain washed cells. The cells were suspended in 35 ml of a cold physiological saline solution. To 8 ml of the suspension were added 600 mg of L-sorbose, 1 ml of 2-(N-morpholino)-ethanesulfonic acid (MES) buffer (pH 6.5, 0.5M) and 360 mg of $CaCO_3$ and the mixture was brought to 20 ml with water. The mixture was incubated with shaking in a 200 ml-flask at 30° C. for 24 hours. The reaction mixture thus obtained contained 21.5 mg/ml of 2-keto-L-gulonic acid (conversion ratio: 66.5% based on used sugar).

EXAMPLE 5

The strain *Pseudomonas sorbosoxidans* 526-21 was grown on a slant at 30° C. for 3 days and the slant contained 2.5% D-sorbit, 1% peptone, 1% yeast extract, 0.2% $CaCO_3$ and 2% agar. A test tube charged 5 ml of PY medium (pH 7.0) containing 0.5% peptone, 0.5% yeast extract and 0.2% NaCl was inoculated with a loopful of cells from the slant and then incubated at 28° C. with shaking for 16 hours.

A portion (2 ml) of the obtained culture broth was added to 1 ml of PY medium containing 1 mg nitrosoguanidine, and then incubated at 28° C. for 30 minutes. The treated cells were centrifuged at 5,000 rpm for 10 minutes, resuspended in 10 ml of fresh PY medium, and again centrifuged at 5,000 rpm for 10 minutes to remove the mutagen. Cells were suspended in 5 ml of PY medium and incubated at 28° C. with shaking for 3 hours. After the obtained culture broth was adequately diluted with PY medium, 0.1 ml of the resultant was spread on plates (diameter: 9 cm) poured with PY medium supplemented with 10% L-sorbose and 2% agar, and then incubated at 28° C. for 7 days. Resulting colonies were transplanted to the slants and incubated at 28° C. for 3 days.

A loopful of cells grown on each of the slants was inoculated into a test tube poured with 3 ml of a medium (pH 6.6) composed of 10% L-sorbose, 2% corn steep liquor, 0.3% dried yeast, 0.02% $Na_2S_2O_3 \cdot 5H_2O$, 0.1% $FeSO_4 \cdot 7H_2O$, 0.3% $(NH_4)_2SO_4$, 0.4% peptone and 4% $CaCO_3$ and incubated at 30° C. with shaking for 5 days.

Each of the obtained culture broths was centrifuged at 12,000 rpm for 5 minutes, and the supernatant was diluted five times with 0.3N HCl, and again centrifuged at 12,000 rpm for 5 minutes.

One $\mu l$ of each of the supernatant obtained was spotted on a cellulose plate (Merk, U.S.A.) and then developed with a solvent of phenol-water-formic acid (75:25:5) at room temperature for 3 hours. This plate was air-dried and then was developed using a silver nitrate reagent. The strain whose supernatant showed the biggest black-brown spot at a Rf value of about 3.0 (2-keto-L-gulonic acid) was selected as the strain SB-15 (IFO 14604, FERM BP-1356).

EXAMPLE 6

The mutant strain SB-15 shown in Example 5 was grown on a slant (pH 7.0) containing 2.5% D-sorbit, 1% peptone, 1% yeast extract, 0.2% $CaCO_3$ and 2% agar at 30° C. for 3 days.

A loopful of the cells was inoculated into a sterile, 200 ml-conical flask which contained 20 ml of a medium (pH 6.8) containing 2% glucose, 1% peptone, 1% yeast extract and 2% $CaCO_3$, and then incubated at 30° C. with shaking (200 rpm) for 2 days to obtain the first seed culture.

The first seed culture (1.5 ml) was transplanted into a 200 ml-flask containing the above-mentioned medium and then incubated at 30° C. for 2 days to obtain the second seed culture.

The second seed culture (2 ml) was transplanted into a sterile, 200 ml-conical flask poured with 25 ml of a fermentation medium containing 0.5% yeast extract, 2% corn steep liquor, 0.1% $FeSO_4 \cdot 7H_2O$, 0.05% $Na_2S_2O_3 \cdot 5H_2O$, 4% $CaCO_3$ and 10% L-sorbose (separately sterilized), and then incubated at 30° C. with shaking for 3 days.

The obtained culture broth was found to contain 82.0 mg/ml of 2-keto-L-gulonic acid (conversion ratio: 76.1% based on used sugar) by subjecting high performance liquid chromatography, while the parent strain 526-21 incubated in the same manner was found to contain 47.1 mg/ml of 2-keto-L-gulonic acid.

EXAMPLE 7

The strain SB-15 was incubated in the same manner as mentioned in Example 6 except for that concentrations of $CaCO_3$ and L-sorbose in the fermentation medium were 6 and 13%, respectively.

The obtained culture broth was found to contain 84.0 mg/ml of 2-keto-L-gulonic acid (conversion ratio: 60.0% based on used sugar) by subjecting high performance liquid chromatography, while the parent strain 526-21 incubated in the same manner was found to contain 63.8 mg/ml of 2-keto-L-gulonic acid.

What is claimed is:

1. A biologically pure culture of a microorganism of *Pseudomonas sorbosoxidans* which is a motile rod bacterium having two or more polar flagella, does not produce dihydroxyacetone from glycerol, contains ubiquinone having 10 isoprene units, and requires thiamine, riboflavin and pantothenic acid for the growth.

2. A biologically pure culture according to claim 1, wherein the microorganism is *Pseudomonas sorbosoxidans* 526-21 (IFO 14501, FERM BP-1334).

3. A biologically pure culture according to claim 1, wherein the microorganism is *Pseudomonas sorbosoxidans* 526-22 (IFO 14502, FERM BP-1335).

4. A biologically pure culture according to claim 1, wherein the microorganism is *Pseudomonas sorbosoxidans* 526-42 (IFO 14503, FERM BP-1336).

5. A biologically pure culture according to claim 1, wherein the microorganism is *Pseudomonas sorbosoxidans* SB-15 (IFO 14604, FERM BP-1356).

* * * * *